United States Patent [19]

Tseng et al.

[11] Patent Number: 4,888,345

[45] Date of Patent: Dec. 19, 1989

[54] 4,8-DISUBSTITUTED-1,2-DIHYDRO AND 1,2,3,4-TETRAHYDROIMIDAZO-[1,5-A] PYRIMIDINES

[75] Inventors: Shin S. Tseng, Bridgewater, N.J.; John P. Dusza, Nanuet; Joseph W. Epstein, Monroe, both of N.Y.

[73] Assignee: American Cyanamid Company, Wayne, N.J.

[21] Appl. No.: 159,977

[22] Filed: Feb. 24, 1988

[51] Int. Cl.$^4$ .................... C07D 487/02; A61K 31/53
[52] U.S. Cl. ..................... 514/258; 544/281
[58] Field of Search ..................... 544/281; 514/258

[56] References Cited

U.S. PATENT DOCUMENTS 4,236,005 11/1980 Dusza et al. ..................... 544/281
4,374,988 2/1983 Dusza et al. ..................... 544/281

OTHER PUBLICATIONS

Chemical Abstracts Index Guide, 1984, p. 2141.

*Primary Examiner*—Mukund J. Shah
*Assistant Examiner*—C. L. Cseh
*Attorney, Agent, or Firm*—Kenneth J. Dow; Edward A. Conroy, Jr.

[57] ABSTRACT

This disclosure describes novel 4,8-disubstituted-1,2-dihydro- and -1,2,3,4-tetrahydro -imidazo-[1,5-a] pyrimidines useful as antihypertensive agents and/or as anxiolytic agents in mammals and as intermediates for the synthesis of biologically active compounds.

16 Claims, No Drawings

4,8-DISUBSTITUTED-1,2-DIHYDRO AND 1,2,3,4-TETRAHYDROIMIDAZO-[1,5-A] PYRIMIDINES

BRIEF SUMMARY OF THE INVENTION

The present invention relates to new organic compounds and more particularly is concerned with novel 4,8-disubstituted-1,2-dihydro and 1,2,3,4-tetrahydroimidazo[1,5-a]pyrimidines useful as antihypertensive agents and/or anxiolytic agents in mammals and as intermediates for the synthesis of biologically active compounds. The compounds of the present invention may be represented by the following structural formula (I):

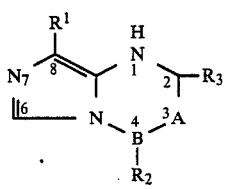

wherein $R_1$ is selected from the group consisting essentially of carbamoyl, cyano and —COO—$R_4$, where $R_4$ is hydrogen, lower alkyl($C_1$–$C_3$) and alkoxyalkyl($C_1$–$C_6$);

$R_2$ is

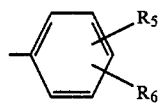

where $R_5$ and $R_6$ may be the same or different and may be selected from the group consisting essentially of hydrogen, halogen, lower alkyl($C_1$–$C_3$), lower alkoxy($C_1$–$C_3$), nitro, trifluoromethyl or morpholino; $R_2$ may also be; $R_3$ is hydrogen or lower alkyl($C_1$–$C_3$); and A—B

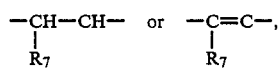

where $R_7$ is hydrogen or lower alkyl($C_1$–$C_3$).

A preferred embodiment of the present invention may be represented by the following structural formula:

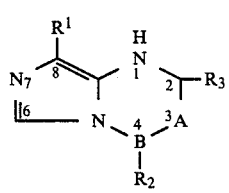

wherein $R_1$ is selected from the group consisting essentially of carbamoyl, cyano and —COO—$R_4$, where $R_4$ is hydrogen, lower alkyl($C_1$–$C_3$) and alkoxyalkyl($C_1$–$C_6$);

$R_2$ is

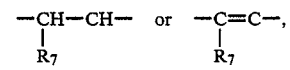

where $R_5$ and $R_6$ may be the same or different and may be selected from the group consisting essentially of hydrogen, halogen, lower alkyl($C_1$–$C_3$), lower alkoxy($C_1$–$C_3$), nitro, trifluoromethyl or morpholino; $R_2$ may also be; $R_3$ is hydrogen and A–B is $$-CH-CH- \quad \text{or} \quad -C=C-,$$
$$\quad\ |\qquad\qquad\qquad\quad\ |$$
$$\quad R_7 \qquad\qquad\qquad\quad R_7$$

where $R_7$ is hydrogen.

The present invention also includes novel compositions of matter containing the above-defined compounds which are useful as antihypertensive agents and/or as anxiolytic agent in mammals and the methods for treating hypertension and meliorating anxiety in mammals therewith. The invention also comprises processes for the preparation of compounds within the scope of the structural formula hereinabove described.

DETAILED DESCRIPTION OF THE INVENTION

The novel compounds of the present invention are obtainable as colorless to yellow crystalline materials having characteristic melting points and absorption spectra. They are generally soluble in organic solvents such as lower alkanols, chloroform, tetrahydrofuran, N,N-dimethylformamide, dichloromethane, dimethylsulfoxide and the like, but are generally insoluble in water.

The novel 4,8-disubstituted-1,2-dihydro and 1,2,3,4-tetrahydroimidazo[1,5-a]pyrimidines of the present invention may be readily prepared as set forth in the following reaction schemes:

Scheme 1

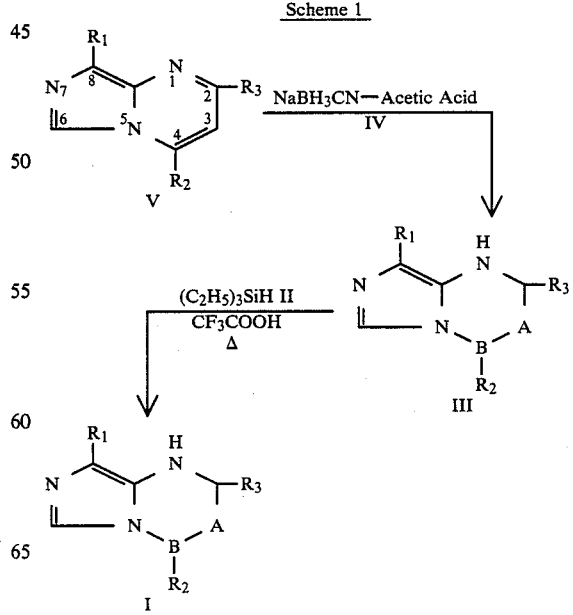

wherein $R_1$, $R_2$ and $R_3$ are as hereinabove defined; and A—B is

in formula III and

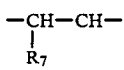

in formula I where $R_7$ is as hereinabove defined.

As shown hereinabove (scheme 1) an imidazo[1,5-a]pyrimidine V (prepared as described in U.S. Pat. Nos. 4,236,005 and 4,374,988), with an electron withdrawing group such as carbamoyl, cyano, carboxyl, carboxyalkyl or carboxyalkoxy in the C8 position and a phenyl, substituted phenyl or heteroaryl group in the C4 position and hydrogen or lower alkyl in the C2 position is reacted with a reducing agent such as sodium cyanoborohydride IV by stirring in glacial acetic acid under nitrogen in an ice bath for approximately one hour, then at room temperature for from 1-48 hours. Evaporation of the solvent in vacuo gives a residue which is treated with water and filtered. The solid is dissolved in an inert solvent such as dichloromethane or acetonitrile and the like and is treated with saturated sodium bicarbonate solution, then washed with water. Separation and evaporation of the organic phase gives the crude dihydro product III, where A—B is

and where $R_7$ is hydrogen or lower alkyl($C_1$-$C_3$) which is recrystallized from a solvent such as ethanol, acetonitrile and the like or from a mixture of solvents such as etherhexane, ethanol-methanol, chloroform-methanol, dichloromethane-hexane and the like.

Scheme 2

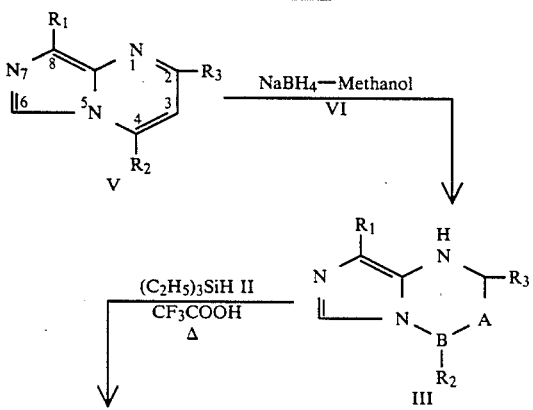

-continued
Scheme 2

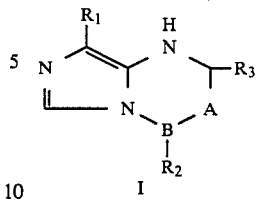

Alternatively as shown hereinabove (scheme 2) an imidazo[1,5-a]-pyrimidine V (prepared as described in U.S. Pat. Nos. 4,236,005 and 4,374,988) may be reacted with sodium borohydride VI in a solvent such as methanol or tetrahydrofuran and the like, or a mixture of solvents such as methanol/tetrahydrofuran and the like by stirring, under nitrogen at room temperature from 1-48 hours. Filtration and evaporation of the filtrate provides a residue which is washed with water, then is dissolved in an inert solvent such as dichloromethane or acetonitrile and the like, dried and purified by conventional means such as chromatography and crystallization.

The dihydro product III is reduced with triethylsilane in trifluoroacetic acid at 55°-65° C. for 1-24 hours according to the procedure of Lanzilotti, et al., J. Org. Chem., 44, 4809 (1979). The reaction mixture at ambient temperature is made slightly basic (pH 9) with aqueous potassium hydroxide to precipitate the crude product I which is then isolated and purified by crystallization or chromatography.

The imidazo[1,5-a]pyrimidine intermediates V are disclosed in U.S. Pat. No. 4,236,005 and 4,374,988. They are prepared by condensation of an appropriately substituted 4-aminoimidazole with an appropriately substituted 3-dialkylaminoacrylophenone. The preferred procedure involves the reaction of the imidazole and the acrylophenone in refluxing glacial acetic acid in the presence of sodium acetate for a period of 2-24 hours.

It has been found that the use of sodiumcyanoborohydride in acetic acid offers a simple, convenient regioselective means for the reduction of imidazo[1,5-a]-pyrimidines and derivatives thereof, bearing functional groups such as halogens, nitriles, amides, amidines, esters and carboxylic acids without reducing these groups and providing the final products in higher yield than obtained with other reducing agents. In fact, certain of the above described functional groups are known to be affected by the use of other reducing agents, with mixtures of products being formed which require the employment of time consuming separation techniques to obtain the desired product.

Another effective means for the reduction of imidazo[1,5-a]-pyrimidines is concerned with the use of sodium borohydride in glacial acetic acid.

Certain of the novel compounds of the present invention are active hypotensive agents at nontoxic doses when administered to mammals. These compounds were tested for hypotensive activity by the method of P. S. Chan and D. Poorvin, Clinical and Experimental Hypertension, 1(6), 817-830 (1979). Male, 16 week old, spontaneously hypertensive rats of the Okamoto strain having an average mean arterial blood pressure of 160±1.5 mm of mercury are used in the test. One to 3 rats are used per test compound. A rat is dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary.

The results of this test on representative compound of the present invention appear below in Table I.

TABLE I

| Reduction of Mean Arterial Blood Pressure in Spontaneously Hypertensive Rats | |
|---|---|
| Compound | MABP/mm Hg (No. of rats) |
| 1,2-Dihydro-4-[3-(trifluoromethyl)phenyl]-imidazo[1,5-a]pyrimidine-8-carboxamide | 111(1) |
| 4-(3-Chlorophenyl)-1,2-dihydroimidazo-[1,5-a]pyrimidine-8-carboxamide | 132(1) |
| 4-(2,5-Dichlorophenyl)-1,2-dihydroimidazo-[1,5-a]pyrimidine-8-carboxamide | 106(1) |
| 1,2-Dihydro-4-phenylimidazo[1,5-a]pyrimidine-8-carboxamide | 121(1) |
| 1,2-Dihydro-4-(3-nitrophenyl)imidazo-[5-a]pyrimidine-8-carboxamide | 139(2) |
| 1,2-Dihydro-4-(3-pyridinyl)imidazo[1,5-a]-pyrimidine-8-carboxamide | 138(1) |

The antianxiety properties of certain of the novel compounds of the present invention have been establish in a test which measures the ability of a test compound to inhibit the binding of tritiated benzodiazepines to brain-specific receptors of mammals. A modification of the method described by R. F. Squires, et al., Nature, 266, No. 21, pg 732 (April 1977) and H. Mohler, et al., Science, 198:849 (1977) was employed.

Male albino rats (Wistar strain, weighing 150 g 200 g each) were used. The test compounds were solubilized in dimethylformamide, acetic acid, ethanol or hydrochloric acid.

Whole cortex of rats was homogenized gently in 20 volumes of ice-cold 0.32 M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen ($-20°$) of use. Frozen $P_2$ preparations were thawed and resuspended in four times the original homogenizing volume at time of assay.

The binding assay consisted of 300 μl of the $P_2$-fraction suspension (0.2–0.4 mg protein), 100 μl of test drug and 100 μl of $^3$H-diazepam (1.5 nM, final concentration) or $^3$H-flunitrazepam (1.0 nM, final concentration) which was added to 1.5 ml of 50 mM Tris.HCl (pH 7.4). Nonspecific binding controls and total binding controls received 100 μl of diazepam (3 μM final concentration) and 100 μl of deionized water, respectively, in place of the test compound. Incubation for 30 minutes proceeded in ice and was terminated by filtration, under vacuum, through glass fiber filters. The filters were washed twice with 5 ml of ice-cold 50 mM Tris.HCl (pH 7.4) and placed in scintillation vials. After drying at 50°–60° C. for 30 minutes, 10 ml of diluent was added and the radioactivity determined in a scintillation counter.

Inhibition of binding was calculated by the difference between total binding and binding in the presence of test compound, divided by the total binding, ×100.

Physiological activity can be shown by a test compound that inhibits $^3$H-benzodiazepine binding by 12% or more. Such in vitro activity is biologically relevant when the test compound also demonstrates statistically significant anxiolytic activity through in vivo studies.

The results of this in vitro test on representative compounds of the present invention are given in Table II.

TABLE II

| Inhibition of the Binding of $^3$H-Benzodiazepine to Brain-Specific Receptors of Rats | |
|---|---|
| Compound | % Inhibition |
| 1,2-Dihydro-4-(3-methoxyphenyl)imidazo-[1,5-a]pyrimidine-8-carboxamide | 27 |
| 1,2-Dihydro-4-[4-(4-morpholinyl)phenyl]-imidazo[1,5-a]pyrimidine-8-carboxamide | 29 |

The novel compounds of the present invention have been found to be highly useful for lowering elevated blood pressure in mammals when administered in amounts ranging from about 2.5 mg to about 100 mg/kg of body weight per day. A preferred dosage regimen for optimum results would be from about 50 mg to about 750 mg per dose. Such dosage units are employed that a total of from about 200 mg to about 3.0 g of the active compound for a subject of about 70 kg of body weight are administered in a 24 hour period.

The novel compounds of the present invention which are effective for alleviating anxiety in warm-blooded animals are administered in amounts ranging from about 0.1 mg to about 35.0 mg/kg of body weight per day. A preferred dosage regimen for optimum results would be from about 0.5 mg to abut 20.0 mg/kg of body weight per day and such dosage units are employed that a total of from about 35 mg to about 1.4 g of the active compound for a subject of about 70 kg of body weight are administered in a 24 hour period.

The dosage regimen for the above-described utilities may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be administered orally, for example, with an inert diluent or with an assimilable edible carrier. They may be enclosed in hard or soft shell gelatin capsules or compressed into tablets. They also may be incorporated directly with the food of the diet. For oral therapeutic administration, these active compounds may be incorporated with excipients and used in the form of tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to abut 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts used. In addition, these active compounds may be incorporated into sustained release preparations and formulations.

These active compounds may also be administered parenterally or intraperitoneally. Solutions or suspensions of these active compounds as a free base or pharmacologically acceptable salt can be prepared in water suitably mixed with a surfactant such as sodium lauryl sulfate or an emulsifier or stabilizer such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following non-limiting examples.

EXAMPLE 1

3-Dimethylaminoacrylophenone

A mixture of 50.0 g of acetophenone and 150 ml cool to room temperature, then the solvent was removed in vacuo to give a crystalline residue. The residue was treated with 400 ml of hexane then filtered. The material on the filter was washed with hexane to give 47.8 g of the desired product as yellow crystals, mp 88°–91° C.

The following 3-(dimethylamino)acrylophenone intermediate compounds listed in Table III were prepared in a manner similar to the above procedure or by those described in U.S. Pat. Nos. 4,178,449; 4,236,005; 4,281,000; and 4,374,988.

TABLE III 3-(Dimethylamino)acrylophenone Intermediates $$R_2-\overset{O}{\underset{\|}{C}}-CH_3 + (CH_3O)_2-\overset{H}{\underset{|}{C}}-N-(CH_3)_2 \longrightarrow R_2-\overset{O}{\underset{\|}{C}}-CH=CHN(CH_3)_2$$

| Ex. | $R_2$ | Product | MP °C. |
|---|---|---|---|
| 2 | 3-Trifluoromethylphenyl | 3-Dimethylamino-3'-(trifluoromethyl)acrylophenone | 59–60 |
| 3 | 3-Chlorophenyl | 3'-Chloro-3-dimethylaminoacrylophenone | 68–70 |
| 4 | 2,5-Dichlorophenyl | 2',5'-Dichloro-3-dimethylaminoacrylophenone | 83–85 |
| 5 | 3-Methoxyphenyl | 3-Dimethylamino-3'-methoxyacrylophenone | Viscous Liquid |
| 6 | 3,4-Dimethoxyphenyl | 3-Dimethylamino-3',4'-dimethoxyacrylophenone | 124–125 |
| 7 | 4-Chlorophenyl | 4'-Chloro-3-dimethylaminoacrylophenone | 83–84 |
| 8 | 4-Methoxyphenyl | 3-Dimethylamino-4'-methoxyacrylophenone | 92–95 |
| 9 | 3,4-Dichlorophenyl | 3',4'-Dichloro-3-dimethylaminoacrylophenone | 94–95 |
| 10 | 3-Nitrophenyl | 3-Dimethylamino-3'-nitroacrylophenone | 109–111 |
| 11 | 4-Methylphenyl | 3-Dimethylamino-4'-methylacrylophenone | 92.5–95 |
| 12 | 3-Pyridinyl | 3-Dimethylamino-1-(3-pyridinyl)-2-propen-1-one | 82–84 |
| 13 | 4-Morpholinophenyl | 3-Dimethylamino-4'-morpholinoacrylophenone | 209–211 |

EXAMPLE 14

4-(3-Chlorophenyl)imidazo[1,5-a]pyrimidine-8-carboxamide

A mixture of 13.9 g of 4-amino-5-imidazolecarboxamide hydrochloride, 24.0 g of 3'-chloro-3-dimethylaminoacrylophenone (U.S. Pat. No. 4,209,621, Ex. 50) and 200 ml glacial acetic acid was heated at reflux for 5 hours. The liquid was evaporated in vacuo to give a yellow solid. The excess acid was neutralized with saturated sodium bicarbonate solution and this mixture was filtered and the solid was washed with water and then was dried. Recrystallization from ethanol-methanol gave 10.2 g of the desired product as yellow crystals, mp 252°–254° C.

EXAMPLE 15

4-(2,5-Dichlorophenyl)imidazo[1,5-a]pyrimidine-8-carboxamide

A stirred mixture of 5.2 g of 4-amino-5-imidazolecarboxamide hydrochloride and 10.0 g of 2',5'-dichloro-3-dimethylaminoacrylophenone (prepared as described in Example 4) in 80 ml of glacial acetic acid was heated at reflux for 4 hours. Evaporation in vacuo gave a dark oil which was dissolved in dichloromethane and treated with saturated sodium bicarbonate. The organic layer was separated, washed with water then dried over anhydrous sodium sulfate. The dichloromethane solution was passed through a short column of hydrous magnesium silicate. Evaporation of the eluate gave a semisolid which was treated with hot dichloromethane-hexane to give a yellow precipitate which was collected by filtration and dried to give 7.3 g of the product of the example, mp 230°–234° C.

EXAMPLE 16

4-Phenylimidazo[1,5-a]pyrimidine-8-carboxamide

A stirred mixture of 11.0 g of 4-amino-5-imidazolecarboxamide hydrochloride and 15.0 g of 3-dimethylaminoacrylophenone (prepared as described in Example 1) in 120 ml of glacial acetic acid was heated at reflux for 4 hours. The solvent was evaporated in vacuo to give a dark oil which was dissolved in dichloromethane, then treated by stirring with saturated sodium bicarbonate. The organic solvent was evaporated and the remaining mixture was filtered and the solid was washed with water, dried, and then was recrystallized from ethanol to give 7.08 g of the desired product as a yellow solid, mp 226°–228° C.

EXAMPLE 17

4-(3-Methoxyphenyl)imidazo[1,5-a]pyrimidine-8-carboxamide

A stirred mixture of 15.0 g of 3-dimethylamino-3'-methoxyacrylophenone (prepared as described in Example 5 and 9.2 g of 4-amino-5-imidazolecarboxamide hydrochloride in 150 ml of glacial acetic acid was heated at reflux for 24 hours. The solvent was evaporated in vacuo and the crystalline residue was treated with 100 ml of saturated sodium bicarbonate solution, filtered and washed with 200 ml of water to give yellow crystals. This material was treated with 400 ml of acetonitrile then with 600 ml of hot ethanol to give 9.9 g of the product of the example as yellow crystals, mp 249°–252° C.

EXAMPLE 18

4-(3,4-Dimethoxyphenyl)imidazo[1,5-a]pyrimidine-8-carboxamide

A stirred mixture of 15.0 g of 3-dimethylamino-3',4'-dimethoxyacrylophenone (prepared as described in Example 6) and 8.0 g of 4-amino-5-imidazolecarboxamide hydrochloride in 150 ml of glacial acetic acid was heated at reflux for 24 hours. The solvent was evaporated in vacuo to give an oil. The oil solidified on standing at room temperature, and this was treated with 200 ml of saturated sodium bicarbonate solution and then it was filtered to collect the crystals. The material was treated by boiling with 700 ml of ethanol and then was filtered. The solid was recrystallized from methanol-chloroform to give 7.9 g of the desired product, mp 262°–265° C.

EXAMPLE 19

4-(4-Chlorophenyl)imidazo[1,5-a]pyrimidine-8-carboxamide

A stirred mixture of 20.0 g of 4'-chloro-3dimethylaminoacrylophenone (prepared as described in Example 7) and 12.0 g of 4-amino-5-imidazolecarboxamide hydrochloride in 450 ml of glacial acetic acid was heated at reflux for 6 hours. The mixture was allowed to stand at room temperature for 16 hours. The solvent was evaporated in vacuo and the crystalline residue was treated with saturated sodium bicarbonate and filtered and then it was washed with water. The crude product was then recyrstallized from ethanol to give 17.0 g of yellow crystals. A 5.0 g amount of this material was heated on a steam bath in 300 ml of ethanol and 700 ml of chloroform, clarified hot with activated charcoal and filtered. The filtrate was evaporated in vacuo to give 4.3 g of the product of the example as yellow crystals, mp 290°–292° C.

EXAMPLE 20

4-(4-Methoxyphenyl)imidazo[1,5-a]pyrimidine-8-carboxamide

A stirred mixture of 15.0 g of 3-dimethylamino-4'-methoxyacrylophenone (prepared as described in Example 8) and 9.2 g of 4-amino-5-imidazolecarboxamide hydrochloride in 450 ml of glacial acetic acid was heated at reflux for 24 hours. Evaporation of the solvent in vacuo gave a solid which was treated with saturated sodium bicarbonate solution, then washed with water and filtered to give colorless crystals. This material was treated with hot acetonitrile and collected by filtration. Recrystallization from ethanol gave 6.1 g of the desired product as yellow crystals, mp 246°–249° C.

EXAMPLE 21

4-(3-Pyridinyl)imidazo[1,5-a]pyrimidine-8-carboxamide

A stirred mixture of 17.7 g of 3-dimethylamino-1-(3-pyridyl)-2-propen-1-one (U.S. Pat. No. 4,281,000, Ex. 1) and 12.6 g of 4-amino-5-imidazolecarboxamide hydrochloride in 100 ml of glacial acetic acid was heated on a steam bath for 4 hours. The reaction mixture was then allowed to stand at room temperature for 16 hours. The mixture was evaporated to dryness in vacuo and the residual solid was partitioned between dichloromethane and saturated sodium bicarbonate. The two layers were separated, the organic layer was dried over anhydrous sodium sulfate and filtered and evaporation of the filtrate gave a dark yellow solid which was treated with isopropyl alcohol. This solid was collected by filtration and washed with hexane. The yellow solid was dried in vacuo to give 10.0 g of the product of the example, mp >260° C.

EXAMPLE 22

4-(3,4-Dichlorophenyl)imidazo[1,5-a]pyrimidine-8-carboxamide

A stirred mixture of 12.0 g of 3',4'-dichloro-3dimethylaminoacrylophenone (prepared as described in Example 9) and 6.3 g of 4-amino-5-imidazolecarboxamide hydrochloride in 450 ml of glacial acetic acid was heated at reflux for 24 hours. The reaction mixture was allowed to stand at room temperature for 16 hours then the mixture was filtered and the crystals that were collected were washed with 300 ml of saturated sodium bicarbonate and then were washed with water. This material was dried, washed with hot methanol and filtered to give 5.9 g of the desired product as yellow crystals, mp 302°–304° C.

EXAMPLE 23

4-(3-Nitrophenyl)imidazo[1,5a]pyrimidine-8-carboxamide

A stirred mixture of 18.0 g of 3-dimethylamino-3'-nitroacrylophenone (prepared as described in Example 10) and 10.30 g of 4-amino-5-imidazolecarboxamide hydrochloride in 450 ml of glacial acetic acid was heated at reflux for 24 hours. Upon standing at room temperature a crystalline precipitate was formed. The precipitate was collected, washed with saturated sodium bicarbonate solution and then with water to give 13.1 g of product. The material was recrystallized from methanol-chloroform by the addition of hexane and by scratching to give 8.7 g of the product of the example as yellow crystals, mp 282°–284° C.

EXAMPLE 24

4-(4-Methylphenyl)imidazo[1,5-a]pyrimidine-8-carboxamide

A mixture of 15.0 g of 3-dimethylamino-4'-methylacrylophenone (prepared as described in Example 11) and 10.0 g of 4-amino-5-imidazolecarboxamide hydrochloride in 150 ml of glacial acetic acid was stirred and heated at reflux for 4 hours. The mixture was evaporated in vacuo to give a yellow crystalline solid. The solid was treated with saturated sodium bicarbonate solution and was collected by filtration, and then it was recrystallized from acetonitrile to give 10.7 g of the desired product as yellow crystals, mp 263°–266° C.

EXAMPLE 25

4-(4-Morpholinyl)phenyl]imidazo[1,5-a]pyrimidine-8-carboxamide

A mixture of 15.0 g of 3-dimethylamino-4'-morpholinoacrylophenone (prepared as described in Example 13) and 7.26 g of 4-amino-5-imidazolecarboxamide hydrochloride in ml of glacial acetic acid was stirred and heated at reflux for 5 hours. The solution was evaporated in vacuo to give a black oil that was then dissolved in dichloromethane and then saturated sodium bicarbonate solution was added. A precipitate was formed which was collected by filtration as a yellow crystalline solid. The solid was triturated with ether then filtered to give 11.3 g of the product of the example as yellow crystals, mp 274°–277° C.

EXAMPLE 26

1,2-Dihydro-4-[3-(trifluoromethyl)phenyl]imidazo-[1,5-a]pyrimidine-8-carboxamide To a solution of 9.2 g of 4-($\alpha,\alpha,\alpha$-trifluoro-m-tolyl-)imidazo[1,5-a]pyrimidine-8-carboxamide (Ex. 28, U.S. Pat. No. 4,236,005) in 100 ml of glacial acetic acid, was added in portions 3.0 g of sodium cyanoborohydride at room temperature under nitrogen. The mixture was stirred at room temperature for 3 hours. The solvent was evaporated in vacuo to give an oil. The oil was triturated with water and a white precipitate formed, and this was collected by filtration, washed with water and then was slurried with saturated sodium bicarbonate solution. The precipitate was again collected by filtration and washed with water. This solid was dissolved in dichloromethane, and then water was added. The organic layer was separated, dried over anhydrous sodium sulfate and filtered. Evaporation of the filtrate gave a yellow solid which was recrystallized from acetonitrile to give 7.0 g of the product of the example as a light yellow solid, mp 192°–194° C.

EXAMPLE 27

4-(3-Chlorophenyl)-1,2-dihydroimidazo[1,5-a]-pyrimidine-8-carboxamide

To a solution of 5.39 g of 4-(m-chlorophenyl)-imidazo[1,5-a]pyrimidine-8-carboxamide (Example 14) in 100 ml of glacial acetic acid, was added in portions 2.8 g of sodium cyanoborohydride at room temperature under nitrogen. The mixture stirred at room temperature for 2 hours. The solvent was evaporated in vacuo to give an oil, and this was dissolved in dichloromethane, then washed with saturated sodium bicarbonate solution, The organic layer was separated, dried over anhydrous sodium sulfate and filtered through a short column of hydrous magnesium silicate. Evaporation of the solvent gave a yellow solid which was recrystallized from acetonitrile to give 3.25 g of the desired product as a yellow solid, mp 182°–184° C.

EXAMPLE 28

4-(2,5-Dichlorophenyl)-1,2-dihydroimidazo[1,5-a]-pyrimidine-8-carboxamide

To a solution of 4.0 g of 4-(2,5-dichlorophenyl)-imidazo[1,5-a]pyrimidine-8-carboxamide (Example 15) in 80 ml of glacial acetic acid, was added in portions 1.8 g of sodium cyanoborohydride at room temperature, under nitrogen. The mixture was stirred at room temperature for 2 hours. The mixture was evaporated to dryness in vacuo and the residue was triturated with water to provide a white precipitate. The precipitate was collected and washed with water and the solid was dissolved in dichloromethane and extracted with saturated sodium bicarbonate solution. The layers were separated. The organic layer was dried over anhydrous sodium sulfate and filtered. Evaporation of the filtrate gave a yellow solid which was recrystallized from acetonitrile-ethanol to give 3.0 g of the product of the example as a light yellow solid, mp 190°–193° C.

Following the general procedure of Examples 26°–28 and reacting the appropriate imidazo[1,5-a]pyrimidine derivative with sodium cyanoborohydride, the dihydro products of Examples 29°–39, listed in Table IV, were obtained.

TABLE IV

| Ex. | Imidazo[1,5-a]pyrimidine Derivative | Dihydro- Product | MP° C. |
|---|---|---|---|
| 29 | 4-Phenylimidazo[1,5-a]pyrimidine-8-carboxamide | 1,2-Dihydro-4-phenylimidazo[1,5-a]-pyrimidine-8-carboxamide | 152–154 |
| 30 | 4-(3-Methoxyphenyl)imidazo[1,5-a]-pyrimidine-8-carboxamide | 1,2-Dihydro-4-(3-methoxyphenyl)-imidazo[1,5-a]pyrimidine-8-carboxamide | 182–184 |
| 31 | 4-(3,4-Dimethoxyphenyl)imidazo[1,5-a]-pyrimidine-8-carboxamide | 4-(3,4-Dimethoxyphenyl)-1,2-dihydro-imidazo[1,5-a]pyrimidine-8-carboxamide | 276–280 |
| 32 | 4-(d4-Chlorophenyl)imidazo[1,5-a]-pyrimidine-8-carboxamide | 4-(4-Chlorophenyl)-1,2-dihydroimidazo-[1,5-a]pyrimidine-8-carboxamide | 255–258 |
| 33 | 4-(4-Methoxyphenyl)imidazo[1,5-a]-pyrimidine-8-carboxamide | 1,2-Dihydro-4-(4-methoxyphenyl)-imidazo[1,5-a]pyrimidine-8-carboxamide | 236–240 |
| 34 | 4-(3,4-Dichlorophenyl)imidazo[1,5-a]-pyrimidine-8-carboxamide | 4-(3,4-Dichlorophenyl)-1,2-dihydro-imidazo[1,5-a]pyrimidine-8-carboxamide | 247–250 |
| 35 | 4-(3-Nitrophenyl)imidazo[1,5-a]-pyrimidine-8-carboxamide | 1,2-Dihydro-4-(3-nitrophenyl)imidazo-[1,5-a]pyrimidine-8-carboxamide | 208–210 |
| 36 | 4-(4-Methylphenyl)imidazo[1,5-a]-pyrimidine-8-carboxamide | 1,2-Dihydro-4-(4-methylphenyl)imidazo-[1,5-1]pyrimidine-8-carboxamide | 232–237 |
| 37 | 4-(3-Pyridinyl)imidazo[1,5-a]-pyrimidine-8-carboxamide | 1,2-Dihydro-4-(3-pyridinyl)imidazo-[1,5-a]pyrimidine-8-carboxamide | 190–193 |

TABLE IV-continued

| Ex. | Imidazo[1,5-a]pyrimidine Derivative | Dihydro- Product | MP° C. |
|---|---|---|---|
| 38 | 4-[4-(4-Morpholinyl)phenyl]imidazo-[1,5a]pyrimidine-8-carboxamide | 1,2-Dihydro-4-[4-(4-morpholinyl)-phenyl]imidazo[1,5-a]pyrimidine-8-carboxamide | 290–293 |

EXAMPLE 39

1,2-Dihydro-4-[3-(trifluoromethyl)phenyl]imidazo[1,5-a]pyrimidine-8-carbonitrile To a stirred mixture of 1.0 g of 4-($\alpha,\alpha,\alpha$,-trifluoro-m-tolyl)imidazo[1,5-a]pyrimidine-8-carbonitrile (prepared as described in U.S. Pat. No. 4,236,005, Ex. 28) in 100 ml of methyl alcohol under nitrogen, at room temperature, was added, one at a time, 3 pellets of sodium borohydride, totaling about 300 mg. The mixture was stirred until the sodium borohydride was consumed and then was allowed to stand at room temperature. A precipitate which formed was filtered off and set aside (A). The filtrate was evaporated to dryness in vacuo. Water was added to the residue, then the mixture was extracted with dichloromethane. The organic solution was dried over anhydrous sodium sulfate then passed through a short column of hydrous magnesium silicate. Evaporation of the eluate with the addition of hexane gave crystals (B). The preceding precipitate (A) and the crystals (B) were combined and recrystallized from ethanol to give 350 mg of the product of the example as colorless crystals, mp 248°–250° C.

EXAMPLE 40

1,2,3,4-Tetrahydro-4-[3-(trifluoromethyl)phenyl]imidazo[1, 5-a]pyrimidine-8-carboxamide A 4.0 g amount of 1,2-dihydro-4-[3-(trifluoromethyl)phenyl]imidazo [1,5-a]pyrimidine-8-carbonitrile (prepared as described in Example 39) in 80 ml of trifluoroacetic acid was heated to 55° C. in an oil bath, with stirring, under nitrogen then 9.0 ml of triethylsilane was added and the mixture was heated at 60°–65° C. for 10 hours. Stirring was continued for 16 hours at room temperature then the mixture was poured carefully into 160 ml of 25% aqueous potassium hydroxide. The solid that formed was collected by filtration and then was dissolved in 300 ml of chloroform. The organic solution was passed through a short column of hydrous magnesium silicate. The eluate was collected and set aside. The material remaining on the hydrous magnesium silicate was then extracted with acetonitrile and the extract was filtered and the filtrate was evaporated to give a semi-solid. This was treated with ether to give 1.2 g of a solid that was recrystallized from isopropyl alcohol to give the product of the example as a white solid, mp 179°–181° C.

We claim:

1. A 4,8-disubstituted-1,2-dihydroimidazo (1,5-a)-pyrimidine of the formula:

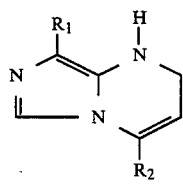

wherein $R_1$ is cyano or carbamoyl and $R_2$ is, a moiety of the formula:

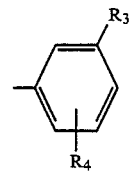

wherein $R_3$ and $R_4$ are each individually selected from the group consisting of hydrogen, halogen, alkyl($C_1$–$C_3$), alkoxy($C_1$–$C_3$), nitro and trifluoromethyl.

2. The compound according to claim 1; 4-(3-trifluoromethylphenyl)-1,2-dihydroimidazo[1,5-a]pyrimidine-8-carboxamide.

3. The compound according to claim 1; 4-(3-chlorophenyl)-1,2-dihydroimidazo[1,5-a]pyrimidine-8-carboxamide.

4. The compound according to claim 1; 4-(2,5-dichlorophenyl)-1,2-dihydroimidazo[1,5-a]pyrimidine-8-carboxamide.

5. The compound according to claim 1; 4-phenyl-1,2-dihydroimidazo[1,5-a]pyrimidine-8-carboxamide.

6. The compound according to claim 1; 4-(3-methoxyphenyl)-1,2-dihydroimidazo[1,5-a]pyrimidine-8-carboxamide.

7. The compound according to claim 1; 4-(3,4-dimethoxyphenyl)-1,2-dihydroimidazo[1,5-a]pyrimidine-8-carboxamide.

8. The compound according to claim 1; 4-(4-chlorophenyl)-1,2-dihydroimidazo[1,5-a]pyrimidine-8-carboxamide.

9. The compound according to claim 1; 4-(4-methoxyphenyl)-1,2-dihydroimidazo[1,5-a]pyrimidine-8-carboxamide.

10. The compound according to claim 1; 4-(3, 4-dichlorophenyl)-1,2-dihydroimidazo[1,5-a]pyrimidine-8-carboxamide.

11. The compound according to claim 1; 4-(3-nitrophenyl)-1,2-dihydroimidazo[1,5-a]pyrimidine-8-carboxamide.

12. The compound according to claim 1; 4-(4-methylphenyl)-1,2-dihydroimidazo[1,5-a]pyrimidine-8-carboxamide.

13. The compound according to claim 1; 4-(3-pyridinyl)-1,2-dihydroimidazo[1,5-a]pyrimidine-8-carboxamide.

14. The compound according to claim 1; 4-(3-trifluoromethylphenyl)-1,2-dihydroimidazo[1,5-a]pyrimidine-8-carbonitrile.

15. The compound 4-(3-trifluoromethylphenyl) 1,2,3,4-tetrahydroimidazo[1,5-a]pyrimidine-8-carboxamide.

16. A therapeutic composition of matter in dosage unit form useful for the treatment of hypertension or anxiety in a mammal which comprises from 5 to 200 mg. per dosage unit of a compound of claim 1 or claim 15 in association with a pharmacologically acceptable carrier.

* * * * *